(12) United States Patent
Hornbaek et al.

(10) Patent No.: US 9,693,578 B2
(45) Date of Patent: Jul. 4, 2017

(54) PROBIOTICS IN FRUIT BEVERAGES

(75) Inventors: Tina Hornbaek, Birkeroed (DK); Caroline Trebbien Gottlieb, Valby (DK); Tina Malling Thorsen, Naestved (DK); Peter Sommer, Frederiksberg (DK)

(73) Assignee: Chr. Hansen A/S, Hoersholm (DK)

( * ) Notice: Subject to any disclaimer, the term of this patent is extended or adjusted under 35 U.S.C. 154(b) by 27 days.

(21) Appl. No.: 13/980,796

(22) PCT Filed: Jan. 23, 2012

(86) PCT No.: PCT/EP2012/050930
§ 371 (c)(1),
(2), (4) Date: Jul. 19, 2013

(87) PCT Pub. No.: WO2012/098254
PCT Pub. Date: Jul. 26, 2012

(65) Prior Publication Data
US 2013/0295226 A1 Nov. 7, 2013

(30) Foreign Application Priority Data

Jan. 21, 2011 (EP) .................................. 11151624
Mar. 15, 2011 (EP) .................................. 11158249

(51) Int. Cl.
*A23L 2/52* (2006.01)
*A23L 2/02* (2006.01)
*C12N 1/20* (2006.01)
*A23L 33/135* (2016.01)

(52) U.S. Cl.
CPC ........ *A23L 2/52* (2013.01); *A23L 2/02* (2013.01); *A23L 33/135* (2016.08); *C12N 1/20* (2013.01); *A23Y 2220/63* (2013.01)

(58) Field of Classification Search
CPC . A23L 2/52; A23L 2/02; A23L 33/135; C12N 1/20; A01B 12/006
USPC .................................................... 426/51, 61
See application file for complete search history.

(56) References Cited

U.S. PATENT DOCUMENTS

| 6,033,691 | A | 3/2000 | Cravero |
| 7,026,161 | B2 * | 4/2006 | Park ...................... A23K 1/008 424/234.1 |
| 7,608,700 | B2 | 10/2009 | Klaenhammer et al. |
| 2005/0220964 | A1 * | 10/2005 | Rizo ....................... A23C 9/133 426/583 |
| 2005/0250135 | A1 | 11/2005 | Klaenhammer et al. |
| 2010/0086646 | A1 | 4/2010 | Francois et al. |
| 2011/0223251 | A1 | 9/2011 | Abrahamsen et al. |

FOREIGN PATENT DOCUMENTS

| CN | 101637291 A | 2/2010 | |
| EP | 0 113 055 | 7/1984 | |
| JP | 2006/025260 | 2/2006 | |
| WO | WO-2004/103083 A1 | 12/2004 | |
| WO | WO 2006/131569 A1 | 12/2006 | |
| WO | WO2008/134626 | * 11/2008 | ............... A23L 1/30 |
| WO | WO-2010/132017 A1 | 11/2010 | |
| WO | WO 2012/036575 A1 | 3/2012 | |

OTHER PUBLICATIONS

Luckow, T. et al. Appetite, 47: 315-323 (2006).*
Doleyres, Y. et al. International Daiy Journal, 2005, 15: 973-988.*
Saarela, M. et al. J. Appl. Microbiol. 2004, 96: 1205-1214.*
MRS—Broth Specification—Difco Manual.*
European Search Report received in EP11158249.0 dated Aug. 2, 2011.
Hee Kyung Park, et al., "Acid Adaptation Promotes Survival of Bifidobacterium breve Against Environmental Stresses", Food and Biotechnology, 1995, pp. 226-230, vol. No. 4.
International Search Report received in PCT/EP2012/050930 dated May 16, 2012.
J.E. Maus, et al., "Employment of stressful conditions during culture production to enhance subsequent cold-and acid-tolerance of bifidobacteria", Journal of Applied Microbiology, 2003, pp. 146-154, vol. 95 No. 1.
N. P. Shah., "Symposium: Probiotic Bacteria" Probiotic Bacteria: Selective Enumeration and Survival in Dairy Foods, J. Dairy Sci., 2000, pp. 894-907, vol. 83 No. 4.
Sudha N., et al., "Studies on the stability and viability of a local probiotic isolate Pediococcus pentosaceus (MTCC 5151) under induced gastrointestinal tract conditions", J. Food Sci Technol., 2006, pp. 677-678, vol. 43 No. 6.
Vivien M. Sheehan, et al., "Assessing the acid tolerance and the technological robustness of probiotic cultures for fortification in fruit juices", Innovation Food Science and Emerging Technologies, 2007, pp. 279-284, vol. 8, No. 2.
Hsin-Yi and Chou, "Acid adaptation and temperature effect on the survival of E. coli O157:H7 in acidic fruit juice and lactic fermented milk product," International Journal of Food Microbiology, No. 70, Oct. 2001, pp. 189-195.
MRS Broth (De Man, Rogosa, Sharpe), "Dehydrated Culture Media," Code: CM0359, Dec. 2014, 1 page.

* cited by examiner

*Primary Examiner* — Hamid R Badr
(74) *Attorney, Agent, or Firm* — Foley & Lardner LLP

(57) ABSTRACT

The present invention relates to a method of producing a probiotic fruit beverage comprising a high viable count of acid-adapted probiotic bacteria, such as strains of *Lactobacillus paracasei* subsp. *paracasei*, and to probiotic fruit beverage obtainable by such method.

17 Claims, 5 Drawing Sheets

PROBIOTICS IN FRUIT BEVERAGES

CROSS-REFERENCE TO RELATED APPLICATIONS

This application is a national phase of PCT/EP2012/050930, filed Jan. 23, 2012, which was published on Jul. 26, 2012, as WO 2012/098254, which claims the benefit of EP Application No. 11151624.1, filed Jan. 21, 2011 and EP Application No. 11158249.0, filed Mar. 15, 2011. The respective contents of these prior applications are incorporated here by reference in their entirety.

FIELD OF INVENTION

The present invention relates to a method for preparing a fruit beverage comprising a high count of live probiotics. The present invention furthermore relates to a probiotic fruit beverage obtainable by such method and use of acid-adapted probiotic bacteria for preparation of a probiotic fruit beverage.

BACKGROUND OF INVENTION

Some bacteria are known to have probiotic properties, i.e. they have a beneficial health effect on the host when ingested in adequate viable amounts. Particularly, bacterial strains belonging to the genera *Lactobacillus* and *Bifidobacterium* have been the subject of many studies demonstrating preventive clinical effects in various fields and on certain physiological functions. These probiotics are generally safe and notably capable of promoting proper operation of the intestinal flora. Besides clear evidence that it has positive effects on the health of the consumer, for a bacterium to fulfil the probiotic definition, it has to be able to survive in and colonize the intestines and survive the harsh processes at production and storage of the food. The clinical evidence indicates that the daily dose of probiotic bacteria should be at least $10^9$ CFU to ensure probiotic efficacy.

The market for probiotic products continues to grow. Probiotics have especially been implemented in dairy products wherein the lactic acid bacteria are relatively well-adapted to the medium. Now orange juices as well as other types of fruit juices and beverages containing pureed fruit and fruit juice have been identified as important vehicles of probiotic cultures which have the benefits of both fruits and probiotics. Additionally, fruit beverages, which contain no milk components, are excellent ways of administration of hypoallergenic probiotics, such as *L. casei* 431® (Chr. Hansen, Hoersholm, Denmark).

However, the rather acidic environment of fruit juices causes a large initial cell count reduction when a reference probiotic bulk is added to e.g. an orange juice. For successful application of probiotic cultures in fruit beverages, appropriate concentrations of probiotic cells have to be ensured during shelf life. Thus, increasing the survival of probiotic cultures in orange juice and other fruit beverages is regarded as very critical.

Methods for producing a fruit beverage containing efficient amounts of live Lactobacilli are known in the art, such as in European Patent EP 0113055, which is related to a method comprising bringing a fruit juice into contact with a solid agent to remove the bacteriostatic components and then proliferating *lactobacillus* in the fruit juice at a pH of 4.0 or lower.

However, in such fruit beverages it is possible to observe bacterial growth and/or activity which induce a production of gas and off-flavor which makes them unsuitable for consumption.

US Patent Application US 2010/0086646 relates to fresh plant juice and/or milk-based food product comprising live probiotics and a dietary protonated weak monoacid with a pH between 3 and 4, the latter prevented probiotics from producing false taste and/or gas in the food product.

PCT Patent Application WO 2010/132017 is directed to a probiotic fruit juice drink comprising at least one strain of probiotic bacteria and at least one gas formation reducer chosen from acerola, pomegranate, cranberry, arqnia, blackcurrant, buckthorn or elderberry.

The addition of monoacids may affect the organoleptic properties of the food product and has also been seen to affect negatively the survival rate of the probiotic bacteria. The addition of acid formation reducers also seems to negatively affect the survival rate of probiotic bacteria. Addition of agents for removal of bacteriostatic compounds and/or for reducing false taste and/or gas in the food product may furthermore prove to be costly.

Thus, there remains a need within the technical field to provide alternative methods for producing probiotic fruit beverages with a high probiotic value, wherein the probiotic fruit beverage exhibits a good taste without off-flavor and gas production, and wherein the probiotic fruit beverage has a long shelf-life. Especially, there is a need for methods which do not involve the addition of solid agents, monoacids or other compounds which may affect the organoleptic qualities of the fruit beverage.

The present invention proposes an alternative method of producing a fruit beverage comprising probiotic bacteria which have been acid-adapted prior to inoculation into the fruit beverage.

SUMMARY OF THE INVENTION

An object of the present invention is to provide a probiotic fruit beverage containing robust probiotic bacteria capable of surviving the acidic environment of the fruit beverage. It is another object of the present invention to provide a probiotic fruit beverage with a good taste. Yet another object of the present invention is to provide such a probiotic fruit beverage which has a long shelf-life.

In order to obtain a high CFU/ml of probiotic bacteria in fruit beverages without the addition of excess amounts of probiotic bacteria the inventors of the present invention have been working on improving the acid-tolerance of the probiotic bacteria thereby rendering the probiotic bacteria robust against low pH.

The present invention is based on the finding that probiotic bacteria may be adapted to acid by propagation without pH stabilization for a certain period of time without significantly affecting the resulting yield in fermentation.

The acid-adapted probiotic bacteria are extremely useful as probiotic compositions for the addition to fruit beverages with a low pH (below 4.2). It combines all the beneficial abilities of the probiotic bacteria with the high nutritional value of the fruits.

The method of the present invention does not involve the addition to the fruit beverage of chemical compounds which could affect the organoleptic qualities of the probiotic fruit beverage.

Accordingly, in a first aspect the present invention relates to a method for producing a probiotic fruit beverage, said method comprising:

(a) acid-adapting at least one strain of probiotic bacteria during propagation;
(b) inoculating a fruit beverage with the at least one strain of acid-adapted probiotic bacteria of step (a); and
(c) optionally packaging the probiotic fruit beverage.

According to one embodiment of the present invention acid-adaptation of the probiotic bacteria in step (a) is carried out by:
 (i) propagating the at least one strain of probiotic bacteria without pH stabilization at a temperature in the range of from 25° C. to 43° C. and preferably from 25° C. to 40° C., in a suitable medium having an initial pH of between about 6.0 and about 7.0, said medium having a composition permitting the medium to reach a pH of between about 5.0 to about 4.0;
 (ii) harvesting the at least one strain of acid-adapted probiotic bacteria;
 (iii) optionally concentrating the at least one strain of acid-adapted probiotic bacteria; and
 (iv) optionally freezing or freeze-drying the at least one strain of acid-adapted probiotic bacteria.

In a preferred embodiment, said medium in step (i) has a composition permitting said medium to reach a pH of between about 5.0 and about 4.0 after at least 8 hours of propagation.

In a still further preferred embodiment the acid-adapted probiotic strain is concentrated in step (iii), i.e. after harvesting the acid-adapted bacteria.

A second aspect of the present invention relates to a probiotic fruit beverage obtainable by the method according to the first aspect. The invention also relates to a probiotic fruit beverage that comprises the strain *Lactobacillus paracasei* subsp. *paracasei* CRL431 (*L. casei* 431®).

A third aspect of the present invention concerns a method for obtaining a culture of an acid-adapted probiotic strain, said method comprising the steps of:
 (a) propagating a probiotic strain without pH stabilization at a temperature in the range of from 25° C. to 43° C., and preferably from 25° C. to 40° C., in a suitable medium having an initial pH of between about 6.0 to about 7.0, said medium having a composition permitting said medium to reach a pH of between about 5.0 to about 4.0;
 (b) harvesting the acid-adapted probiotic strain;
 (c) optionally concentrating the acid-adapted probiotic strain; and
 (d) optionally freezing or freeze-drying the acid-adapted probiotic strain.

In a preferred embodiment, said medium in step (a) has a composition permitting said medium to reach a pH of between about 5.0 and about 4.0 after at least 8 hours of propagation.

In an especially preferred embodiment the acid-adapted probiotic strain is concentrated in step (c) i.e. after harvesting the acid-adapted probiotic bacteria.

A fourth aspect relates to a culture of an acid-adapted probiotic strain obtainable by a method according to the third aspect of the invention.

A fifth aspect concerns use of a culture of an acid-adapted probiotic strain according to the fourth aspect of the invention for the production of a probiotic fruit beverage.

DETAILED DISCLOSURE

Definitions

Figure 1:
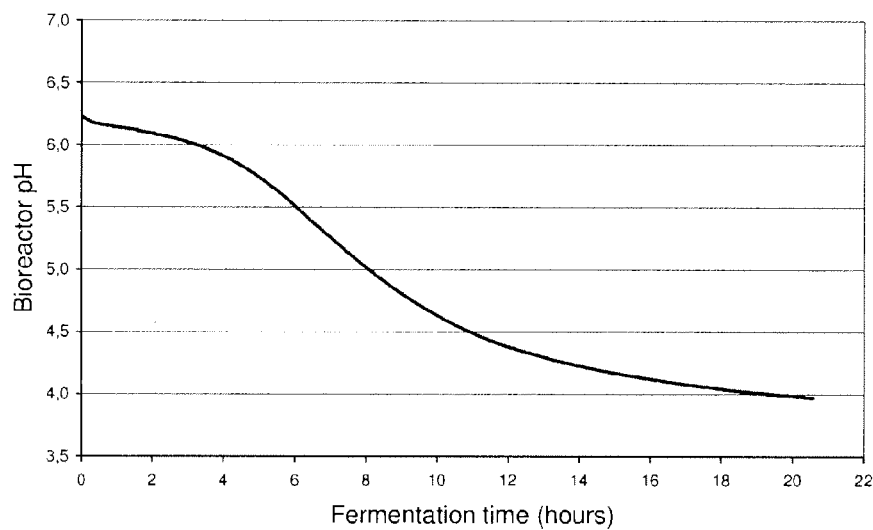
FIG. 1 illustrates acidification of MRS medium (Difco) by *L. casei* 431®. Acid adapted cells were harvested at pH 5.0, pH 4.5, and pH 4.0 by centrifugation.

In the present context the term "fruit juice" refers to the liquid naturally contained in fruit prepared by mechanically squeezing or macerating fresh fruits without the presence of heat and solvents. The "fruit juice" may consist of juice from one type of fruit or a mixture of more than one type of fruit.

The term "fruit drink" in the present context refers to a beverage having a fruit juice content of between 0 to 29%.

The term "nectar" in the present context refers to a beverage having a fruit juice content of between 30 to 99% fruit juice.

In the present context the term "puree" refers to fruits prepared by grounding, pressing and/or straining into the consistency of a thick liquid or a soft paste without the presence of heat and solvents. "Puree" is made of 100% fruit as opposed to being made from just the juice of the fruit.

In the present context the term "fruit beverage" refers to a beverage comprising fruit juice, fruit concentrate and/or fruit puree. The term "fruit beverage" covers "fruit juice", "fruit drink" and "nectar" as defined herein. The "fruit beverage" may be either one containing pulp, or one from which the pulp has been removed by such an operation as centrifugation. The fruit beverages may further contain e.g. oat, soy, almond, whey and/or non-fermented milk, e.g. in the form of milk powder. In a particularly preferred embodiment, the fruit beverages of the invention do not contain dairy components, such as milk.

In the present context the term "acid-adapted" (bacteria) refers to live bacteria which are made tolerant to low pH by gradual exposure to dropping pH levels during cultivation. Accordingly, the process of acid-adapting probiotic bacterial strains generally includes the culturing of these strains in the presence of gradually decreasing pH levels, e.g. until a pH of between 4.0 and 5.0 is reached. Preferably, the probiotic bacteria which are subjected to acid-adaption themselves produce acid during their propagation which accumulates in the medium. More preferably, the acid-producing probiotic bacteria belong to the group of lactic acid bacteria. Alternatively, where the probiotic bacteria which are subjected to acid-adaption do not naturally produce acid, lowering of the pH can also be achieved by external addition of an acid.

The process of acid-adaptation is preferably performed by propagating the probiotic bacteria in a medium without pH stabilization. The expression "without pH stabilization" means that no measures are taken to counteract the gradually decreasing pH. For example, in one embodiment, the medium which is inoculated with the probiotic bacteria does normally not contain buffering agents that could keep the pH stable upon the formation or addition of acid. Alternatively, where the starting medium contains a certain concentration of buffering agents, culturing can be continued until the capacity of the buffering agent is exhausted, and no additional buffering agents are added during culturing. In particular, no basic compounds are added during culturing to neutralise the decreasing pH.

By "off-flavor" is meant an abnormal taste of the food product. The off-flavor is unpleasant for the consumer and therefore not sought. So-called "positive" notes may also be detected in the product, such as for example notes of the fruit type. As these tastes are not unpleasant for the consumer, they are not comprised in the "off-flavor" according to the present invention.

In the present context, the term "packaging" the probiotic fruit beverage relates to the final packaging of the probiotic fruit beverage to obtain a product that can be ingested by e.g. a person or a group of persons. A suitable package may thus be a bottle or carton or similar, and a suitable amount may be e.g. 10 ml to 5000 ml, but it is presently preferred that the amount in a package is from 50 ml to 1000 ml, such as from 200 ml to 1000 ml.

The term "probiotic bacteria" refers to viable bacteria which are administered in adequate amounts to a consumer for the purpose of achieving a health-promoting effect in the consumer. Probiotics can be administered as discrete dosage form, e.g. as capsules, suspensions, and the like. Alternatively, probiotic bacteria are administered in the form of a food or dietary supplement. Probiotic bacteria are capable of surviving the conditions of the gastrointestinal tract after ingestion and colonize the intestine of the consumer. Different types of bacteria have been used in the art as probiotic bacteria, including bacteria of the genus *Lactobacillus*, such as *Lactobacillus acidophilus, Lactobacillus paracasei, Lactobacillus rhamnosus, Lactobacillus casei, Lactobacillus delbrueckii, Lactobacillus lactis, Lactobacillus plantarum, Lactobacillus reuteri* and *Lactobacillus johnsonii*, the genus *Bifidobacterium*, such as the *Bifidobacterium animalis, Bifidobacterium breve, Bifidobacterium infantis, Bifidobacterium longum*, and the like. Probiotic strains have also been described from other genera, such as *Escherichia* and *Bacillus*.

In the present context, the term "mutant" should be understood as a strain derived, or a strain which can be derived from a strain of the invention (or the mother strain) by means of e.g. genetic engineering, radiation and/or chemical treatment. The mutant can also be a spontaneously occurring mutant. It is preferred that the mutant is a functionally equivalent mutant, e.g. a mutant that has substantially the same, or improved, properties (e.g. regarding flavor, post acidification, acidification speed, and/or capability to be acid-adapted) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain.

In the present context, the term "variant" should be understood as a strain which is functionally equivalent to a strain of the invention, e.g. having substantially the same, or improved, properties e.g. regarding flavor, post acidification, acidification speed, and/or capability to be acid-adapted). Such variants, which may be identified using appropriate screening techniques, are a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and Aspects of the Invention

Probiotic bacteria strains, such as those of the genera *Lactobacillus* and *Bifidobacterium*, can be used in beverages. However, they are sensitive to acidic environments and the viable cell count is reduced rapidly when inoculated into medium of pH 4.2 or lower.

The inventors of the present invention surprisingly observed that by acid-adapting a probiotic bacteria strain it significantly increased its survival in fruit beverages, which generally have a low pH in the range of 3-4 due to the fruit acid. In fruit beverages the viability of the acid-adapted probiotic bacteria were essentially unaffected by the low pH for up to 10 weeks cold storage and the high viability in acidic environments were maintained during frozen storage of the bacteria.

Additionally, no off-flavors were detected when the acid-adapted probiotic bacteria were added to fruit beverages, such as fruit beverages of red fruit, tropical fruit and strawberry/banana.

Thus, the present invention in a first aspect relates to a method for producing a probiotic fruit beverage by inoculating a fruit beverage with at least one strain of acid-adapted probiotic bacteria.

Examples of fruit beverages suitable for use in the present invention are those having low pH values, particularly those comprising juices of citrus fruits such as orange juice, grape fruit juice, lime juice and mandarin juice and mixtures thereof. Other examples of fruit beverages include fruit beverages comprising apple juice.

The fruit beverages suitable for the use in the present invention may e.g. be fruit juices, fruit juices from concentrate, fruit drinks and fruit nectar optionally comprising fruit purees and/or water.

The total content of fruit juice and/or fruit puree in the fruit beverage is generally between about 20% to about 99.99% by weight, preferably between about 30% to 95% by weight, more preferably between about 40% to 90% by weight, still more preferably between about 50% to 80% by weight, and most preferably 60% to 70% by weight.

In one embodiment, the fruit beverage of the present invention contains substantially no milk components but may comprise vegetable juice, vegetable concentrate and/or vegetable puree.

In one embodiment the pH of these fruit beverages is in the range of between 3.2 and 4.2, preferably between 3.5 and 3.9.

In one preferred embodiment the fruit beverage in whole or in part is made from fruits selected from the group consisting of strawberry, banana, grape, orange, apple, mango, peach, blueberry, pineapple, lime, raspberry and blackcurrant and mixtures thereof.

According to a preferred embodiment of the invention the fruit beverage comprises strawberry puree, banana puree, grape juice, orange juice, mango puree, peach puree and blueberry puree.

According to another preferred embodiment of the invention the fruit beverage comprises pineapple juice, orange juice, banana puree, mango puree and lime juice.

According to yet another preferred embodiment of the invention the fruit beverage comprises raspberry puree, blackcurrant juice, blueberry puree, grape juice, strawberry puree and banana puree.

The at least one probiotic bacteria is acid-adapted in a suitable medium by propagation without pH stabilization. In one embodiment the at least one probiotic bacteria is propagated without pH stabilization at a temperature in the range from 25° C. to 43° C., preferably in the range from 25° C. to 40° C. in a medium having an initial pH of between about 6.0 and about 7.0, said medium having a composition permitting the medium to reach a pH of between about 5.0 and about 4.0, preferably after at least 8 hours of propagation, thereby producing at least one strain of acid-adapted probiotic bacteria; the at least one strain of acid-adapted probiotic bacteria is harvested; the at least one strain of acid-adapted probiotic bacteria is preferably concentrated; and the at least one strain of acid-adapted probiotic bacteria is optionally frozen or freeze-dried.

The medium used for acid-adapting the probiotic bacteria preferably has a composition which allows said medium to reach a pH of between about 5.0 and about 4.0 during propagation of the probiotic bacteria. This means that the pH of the medium decreases due to the production of acid by the probiotic bacteria, or, alternatively, by a continuous or stepwise addition of acid to the culture. Accordingly, the medium does not contain any essential components which would decompose or otherwise become ineffective or even toxic at a pH between about 5.0 and about 4.0. Essential components of the medium are compounds that are required for the propagation of probiotic bacteria, such as nutrients, carbon and nitrogen sources, vitamins and the like.

The medium used for propagation in a preferred embodiment comprises at least 0.4% yeast extract and at least 2% sugar.

Suitable media that can be used for the propagation of probiotic bacteria, in particular lactic acid bacteria, are well known in the art. For example, if the probiotic bacteria to be used are lactic acid bacteria, any commercially available culture media for lactic acid bacteria may be used, such as Lactobacilli MRS (de Man, Rogosa and Sharpe) medium. An exemplary MRS medium that can be used for the propagation of probiotic bacteria contains 1.0% peptone, 0.8% meat extract, 0.4% yeast extract, 2.0% glucose, 0.5% sodium acetate trihydrate, 0.1% polysorbate 80 (also known as Tween 80), 0.2% dipotassium hydrogen phosphate, 0.2% triammonium citrate, 0.02% magnesium sulphate heptahydrate and 0.005% manganese sulphate tetrahydrate, pH of 6.0-7.0 at 25° C. When using this medium for acid-adapting probiotic bacteria, it is particularly preferred that the dipotassium hydrogen phosphate component is omitted so that the medium is unable to provide for a stable pH despite upon acid production by the bacteria or upon external addition of acid. In an even more preferred embodiment, both the dipotassium hydrogen phosphate component and the sodium acetate trihydrate component are omitted from the above MRS medium. However, as outlined elsewhere herein, it is also possible to maintain buffering components in the media used for acid-adapting probiotic bacteria. In this case, the pH drop will occur after the buffer capacity has been exhausted. The culturing of the probiotic bacteria will not include any external addition of bases.

Generally, the skilled person will know of suitable media for propagation of probiotic bacteria. The above media, with or without buffer components, are suitable for the propagation in starter cultures, such as starter cultures having a volume of about 100 mL, about 500 mL, about 1000 mL, about 2000 mL, about 4000 mL or more, as well as for large scale bacterial cultures, such as cultures in a volume of more than 50 L, more than 100 L, more than 200 L, or more than 400 L. Such large-scale cultures will typically be carried out in a fermenter. The use of a suitable medium is exemplified below in Example 1.

The initial pH of the medium is the pH of the medium prior to addition of probiotic bacteria. In a preferred embodiment the initial pH of the medium is between about 6.0 and 7.0, preferably between about 6.2 and about 6.6.

In one embodiment of the invention the medium reaches the pH of between about 5.0 and about 4.0, preferably after at least 6 hours, at least 8 hours, at least 10 hours of propagation of probiotic bacteria, and more preferably after at least 12 hours of propagation of probiotic bacteria. In a particularly preferred embodiment, the medium reaches the pH of between about 5.0 and about 4.0 after at least 8 hours.

Probiotic bacteria may cause a drop in the pH during propagation due to the production of lactic acid during fermentation. In a preferred embodiment, the medium used in the method of the present invention allows this pH drop, because it does not or essentially does not contain any buffering agents which would keep the pH stable despite the formation of lactic acid during propagation.

Preferably, the probiotic bacteria are propagated without pH stabilization at a temperature in the range from 25° C. to 43° C., preferably in the range from 25° C. to 40° C., more preferably in the range from 30 to 40° C., and most preferably at about 37° C.

In a preferred embodiment of the present invention the at least one strain of probiotic bacteria belongs to the genera *Lactobacillus* or *Bifidobacterium*.

In a more preferred embodiment of the present invention the at least one strain of probiotic bacteria belongs to the species *Lactobacillus paracasei*. If *Lactobacillus paracasei* is used, the temperature for propagation preferably is 37 or 38° C.

The strain *Lactobacillus paracasei* subsp. *paracasei* CRL431 (*L. casei* 431®) was deposited according to the Budapest Treaty on the International Recognition of the Deposit of Microorganisms for the Purposes of Patent Procedure with the American Tissue type Collection Center, 10801 University Blvd, Manassas, Va. 20110, USA on 24 Jan. 1994 under accession number ATCC 55544. The well-known probiotic bacterium is commercially available from Chr. Hansen A/S, 10-12 Boege Alle, DK-2970 Hoersholm, Denmark, under the product name Probio-Tec® F-DVS *L. casei*-431®, Item number 501749, and under the product name Probio-Tec® C-Powder-30, Item number 687018.

In an even more preferred embodiment of the present invention the at least one strain of probiotic bacteria is selected from the group consisting of *Lactobacillus paracasei* subsp. *paracasei* strain CRL431 (*L. casei* 431®) that was deposited with the American Tissue Type Collection Center under accession number ATCC55544, a mutant thereof and a variant thereof.

Methods for harvesting and concentrating the acid-adapted probiotic bacteria are well known in the art. For example, harvesting of the bacteria may be achieved by centrifugation of the bacterial cultures to remove the culture media supernatant. The centrifugation will be gentle enough to avoid breakage of the bacteria. Methods for harvesting cells by centrifugation are commonly known and include, e.g. centrifugation at 2000 to 6000×g for 2-20 minutes. The bacteria may also be harvested by other techniques that have been described in the context of bacterial fermentation, such as filtration, e.g. cross-filtration filtration. Methods for concentration are likewise known in the art. For example, concentration of the bacteria may be achieved by centrifugation and subsequent resuspension in a smaller volume, freeze-drying or membrane filtration techniques, such as filtration through columns or filters.

Generally, the fruit beverage is inoculated with the at least one strain of acid-adapted probiotic bacteria in an amount (initial CFU/ml) of from about $1\times10^4$ to $1\times10^{10}$ CFU/ml, more preferably in an amount from about $1\times10^5$ to $1\times10^9$ CFU/ml, and even more preferably in an amount from about $1\times10^6$ to $1\times10^8$ CFU/ml.

Surprisingly, the viability of the probiotic bacteria is particularly high after the above described adaptation to acidic conditions and will stay high after a storage time of several months at a temperature of 4-10° C. The viability of the at least one strain of acid-adapted probiotic bacteria in one embodiment is at least 50% of the initial CFU/ml after storage for at least 30 days at a temperature of 8° C. in the fruit beverage, such as after at least 42 days of storage at a temperature of 8° C., such as after at least 70 days of storage at a temperature of 8° C.

In a preferred embodiment the viability of the at least one strain of acid-adapted probiotic bacteria is at least 60% of the initial CFU/ml, preferably at least 70% of the initial CFU/ml, and more preferred at least 80% of the initial CFU/ml under the above-mentioned conditions of storage.

Measuring the viable cell count is done by quantifying the number of colony forming units (CFU) in serial dilutions by colony counting on agar plates, according to standard methods in the art. Suitable medium and incubation conditions are given in the Examples below.

After harvesting and/or concentrating, the acid-adapted bacteria are optionally frozen or freeze-dried. For example, the probiotic bacteria may be frozen at about −20° C., preferably at about −80° C., or lower. The freezing procedure is preferably carried out as quickly as possible, preferably by shock-freezing, to avoid cellular damage. Shock-freezing may e.g. be carried out be dumping a vessel containing the bacteria into liquid nitrogen. Thus, in a particularly preferred embodiment the acid adapted probiotic bacteria are shock frozen at about −196° C. Methods for freeze-drying are also well known in the art. During freeze-drying the material is frozen and then the surrounding pressure is reduced to allow the frozen water in the material to sublimate directly from the solid phase to the gas phase. After freezing or shock-freezing the acid-adapted bacteria, the bacteria may be stored at about −20° C., at about −55° C., at about −80° C., or in liquid nitrogen at −196° C. It is particularly preferred to store the acid-adapted bacteria at about −55° C.

According to an embodiment of the present invention, the probiotic fruit beverage is conveniently packaged in a sealed package that contains from 10 to 5000 ml of the product, such as from 50 to 1000 ml or from 200 to 1000 ml.

In a second aspect the present invention relates to a probiotic fruit beverage obtainable by the method according to the first aspect of the invention, wherein the probiotic fruit beverage comprises at least one strain of acid-adapted probiotic bacteria.

In one embodiment the at least one strain of probiotic bacteria is present in the fruit beverage in an amount from about $1\times10^4$ to $1\times10^{10}$ CFU/ml, more preferably in an amount from about $1\times10^5$ to $1\times10^9$ CFU/ml, and even more preferably in an amount from about $1\times10^6$ to $1\times10^8$ CFU/ml after at least 30 days of storage at a temperature of 8° C., such as after at least 42 days of storage at a temperature of 8° C.

Measuring the viable cell count is done by quantifying the number of colony forming units (CFU) in serial dilutions by colony counting on agar plates, according to standard methods in the art. Suitable medium and incubation conditions are given in the Examples below.

In a third aspect the present invention is directed to a method for obtaining a culture of an acid-adapted probiotic strain by propagation without pH stabilization. In a preferred embodiment the probiotic bacteria are propagated without pH stabilization at a temperature in the range from 25° C. to 43° C., more preferably in the range from 25° C. to 400 in a medium having an initial pH of between about 6.0 and about 7.0, said medium having a composition permitting the medium to reach a pH of between about 5.0 and about 4.0 after at least 8 hours of propagation, thereby producing the acid-adapted probiotic bacteria; the acid-adapted probiotic bacteria are harvested; the acid-adapted probiotic bacteria are concentrated; and the acid-adapted probiotic bacteria are optionally frozen or freeze-dried.

In one preferred embodiment the medium comprises at least 0.4% yeast extract and at least 2% sugar.

The initial pH of the medium is the pH of the medium prior to addition of probiotic bacteria. In a preferred embodiment the initial pH of the medium is between about 6.2 and about 6.6.

In a preferred embodiment of the invention the medium reaches the pH of between about 5.0 and about 4.0 after at least 10 hours of propagation of probiotic bacteria, preferably after at least 12 hours of propagation of probiotic bacteria.

In a preferred embodiment the probiotic bacteria belong to the genera *Lactobacillus* or *Bifidobacterium*.

In a more preferred embodiment of the present invention the at least one strain of probiotic bacteria belongs to the species *Lactobacillus paracasei*.

In an even more preferred embodiment of the present invention the at least one strain of probiotic bacteria is selected from the group consisting of *Lactobacillus paracasei* subsp. *paracasei* strain CRL431 (*L. casei* 431®) that has been deposited with the American Tissue Type Collection under accession number ATCC55544, a mutant thereof and a variant thereof.

A fourth aspect of the present invention relates to a culture of an acid-adapted probiotic bacteria strain according to the third aspect of the invention.

A fifth aspect is directed to use of a culture according to the fourth aspect for the production of a probiotic fruit beverage.

In one preferred embodiment the probiotic fruit beverage has a pH of at the most 4.2.

The present invention is further illustrated by the following non-limiting examples.

EXAMPLES

Example 1

Production of Acid Adapted *L. casei* 431®

MRS medium from Difco (ref. 288110) was inoculated 1% (V/V) with *L. casei* 431® from a frozen stock. The culture was grown overnight at 37° C. until pH was lower than 3.9 and stored at 5° C. until use. This overnight culture was used for inoculating 4 L (1%, V/V) of MRS medium (Difco) and incubated overnight at 37° C. until pH was lower than 3.9 and stored at 5° C. until use. This pre-inoculation step was done in order to obtain a sufficient amount of inoculum for the fermentation. A bioreactor containing 400 L of a suitable medium at 10° C. was inoculated with the entire volume of pre-inoculum. The fermentation was initiated by increasing the temperature to 35° C. and the fermentation was followed by monitoring the decrease in pH as an indication of the metabolism of carbohydrate into lactic acid production. During this drop in pH the cells gradually adapt to the low pH. The acid adapted cells were harvested at pH 5.0, 4.5, and 4.0 by centrifugation. The fermentation time was between 10-17 hours depending on the harvest point (FIG. 1).

The concentrated cell mass was instantly frozen in liquid nitrogen (−196° C.) and stored at −55° C. until use.

Example 2

Optimization of Harvest Criteria for Acid Adapted *L. casei* 431®

Figure 2:
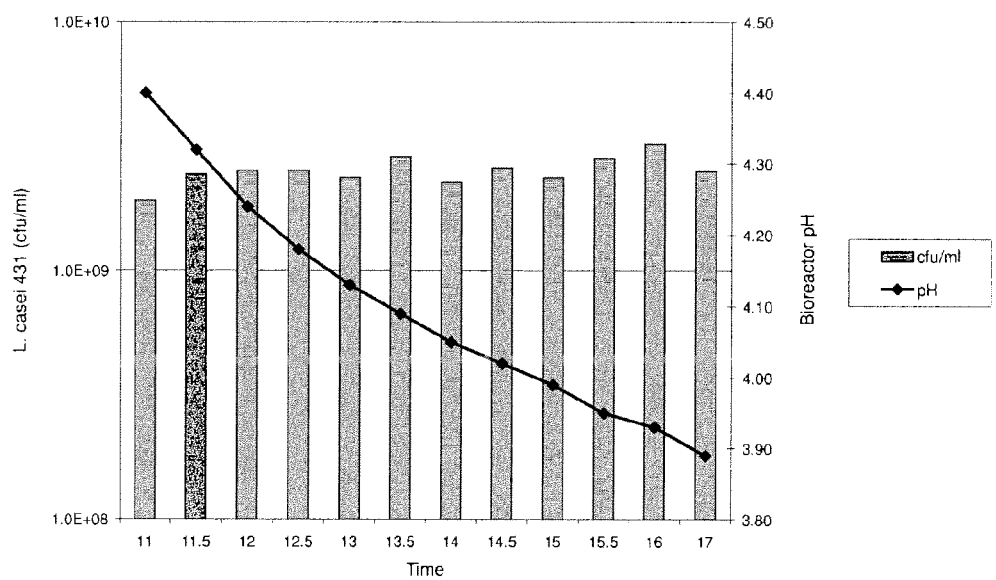
FIG. 2 depicts cell counts of *L. casei* 431® during large scale production.

In order to obtain a maximum number of viable cells, the optimal harvest criterion was determined as follows. A bioreactor was inoculated with pre-inoculum and the fermentation was initiated as described in example 1. Samples of fermentate were taken every 30 minutes from 11 hours post-inoculation (corresponding to pH 4.5) until pH was below 4.0 and the viability was evaluated by determining the number of colony-forming units (CFU) (FIG. 2). CFU was determined by pour plating appropriate ten-fold dilutions in MRS agar followed by anaerobic incubation for 3 days at 37° C.

Cell counts increased until 12 h post-inoculation (corresponding to a pH of 4.24) and remained at a constant level throughout the fermentation. This indicates that the cells are robust and remain viable even when pH drop below 4.0. A pH<4.0 was determined as the optimal harvest criterion providing a sufficient amount of acid adapted and viable cells within a feasible process time.

Example 3

Survival and Organoleptic Quality of Various Fruit Beverages Added Adapted *L. casei* 431®

*L. casei* 431® produced according to the procedure described in example 1 was used for inoculation of different fruit based beverages composed of the following ingredients:

Strawberry and Banana Juice (pH 3.75)
31% strawberry puree
26% banana puree
Grape juice, orange juice, mango puree, peach puree and blueberry puree up to 100%
Tropical Juice (pH 3.88)
32% pineapple juice
32% orange juice
26% banana puree
7% mango puree
3% lime juice
Red Fruit Juice (pH 3.55)
16% of different red fruits (raspberry puree, blackcurrant juice, blueberry puree)
Grape juice, strawberry puree and banana puree up to 100%

F-DVS of the probiotic culture was diluted in saline peptone to ensure that initial cell counts of either $5\times10^7$ or $1\times10^8$ CFU/ml were obtained by adding an inoculum of 1% v/v to cartons of the different fruit juices. The juices were inoculated with *L. casei* 431® adapted to pH 4.0 or pH 5.0 and as a control, the non-adapted *L. casei* 431®. As a control for sensory analysis, cartons were inoculated with the same volume of saline peptone. The inoculated juices were stored protected from light at 8° C. Cell counts of *L. casei* 431® were regularly determined by pour plating appropriate ten-fold dilutions in MRS agar followed by anaerobic incubation for 3 days at 37° C. Sensory evaluations were carried out by a panel of 3 trained sensory assessors during storage.

Figure 3:
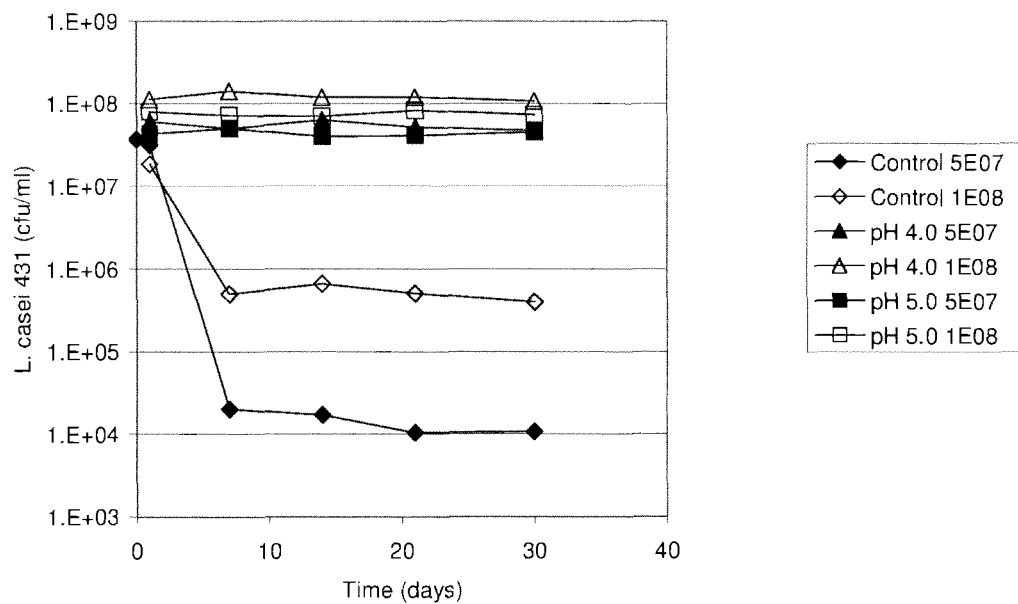
FIG. 3 illustrates cell counts of *L. casei* 431® when added to a strawberry/banana juice for non-adapted (diamond), alternatively adapted either to pH 4.0 (triangle) or pH 5.0 (square) during production and then added in low ($5\times10^7$ CFU/ml, closed symbols) or high ($1\times10^8$ CFU/ml, open symbols) concentrations.
Figure 4:
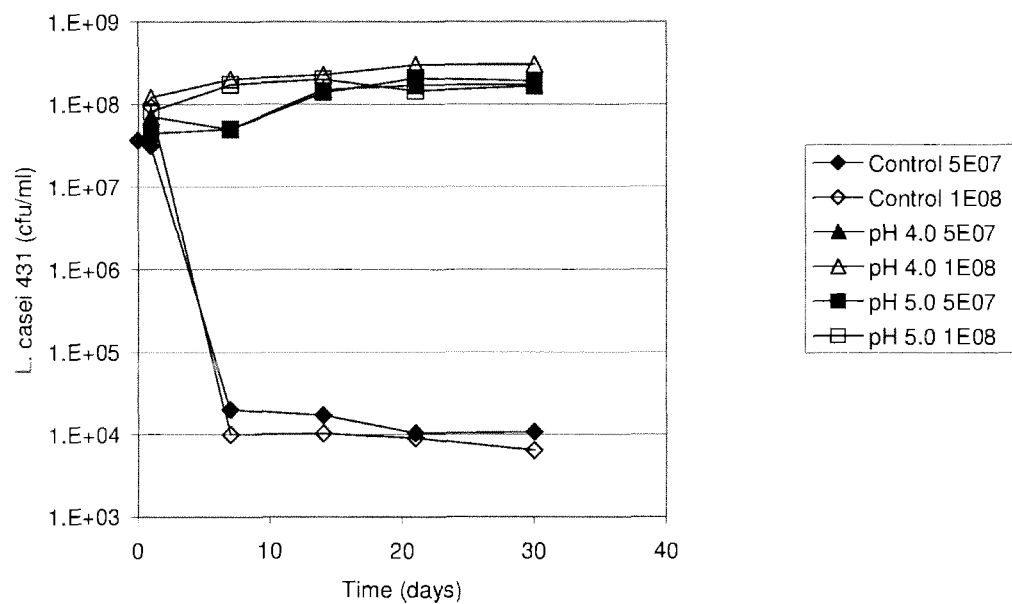
FIG. 4 depicts cell counts of *L. casei* 431® when added to a tropical juice for non-adapted (diamond), alternatively adapted either to pH 4.0 (triangle) or pH 5.0 (square) during production and then added in low ($5\times10^7$ CFU/ml, closed symbols) or high ($1\times10^8$ CFU/ml, open symbols) concentrations.
Figure 5:
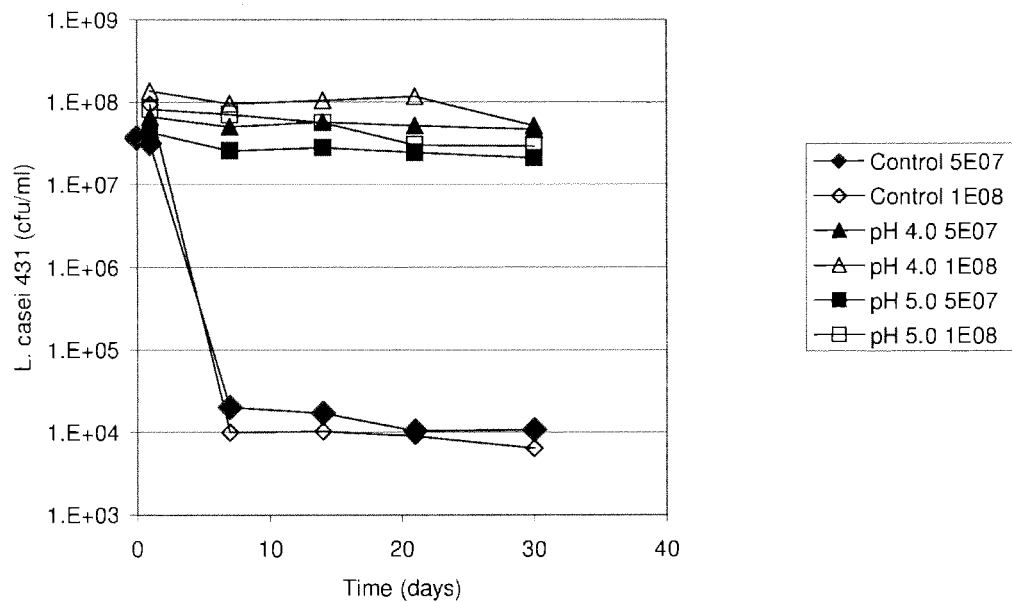
FIG. 5 shows cell counts of *L. casei* 431® when added to a red fruit juice for non-adapted (diamond), alternatively adapted either to pH 4.0 (triangle) or pH 5.0 (square) during production and then added in low ($5\times10^7$ CFU/ml, closed symbols) or high ($1\times10^8$ CFU/ml, open symbols) concentrations.

Cell counts of *L. casei* 431® in the different juices are illustrated in FIGS. 3, 4 and 5. Acid-adapted *L. casei* 431® bacteria were unaffected by storage for at least 30 days in acidic environment of pH 3.5-3.9 whereas non-adapted *L. casei* 431® bacteria had a 1000-fold lower viability in the fruit beverages.

Sensory evaluations during 30 days storage showed no organoleptic changes in neither of the fruit beverages added L. casei 431® compared to the same fruit beverages added a corresponding volume of saline peptone.

Example 4

Survival of L. casei 431® in Orange Juice when Adapted to Three Different pH Values L. casei 431® produced according to the procedure described in example 1 was used for inoculation of 100% orange juice (pH 3.8). F-DVS of the probiotic culture was diluted in saline peptone to ensure that initial cell counts of $1.5 \times 10^8$ CFU/ml were obtained by adding an inoculum of 1% v/v to cartons of orange juice. The juices were either inoculated with L. casei 431® adapted to pH 4.0, pH 4.5 or pH 5.0, and as a control, the non-adapted L. casei 431®. The juices were stored protected from light at 8° C. for 42 days and regularly sampled for cell count determination by pour plating appropriate 10-fold dilutions in MRS agar followed by anaerobic incubation for 3 days at 37° C.

Figure 6:
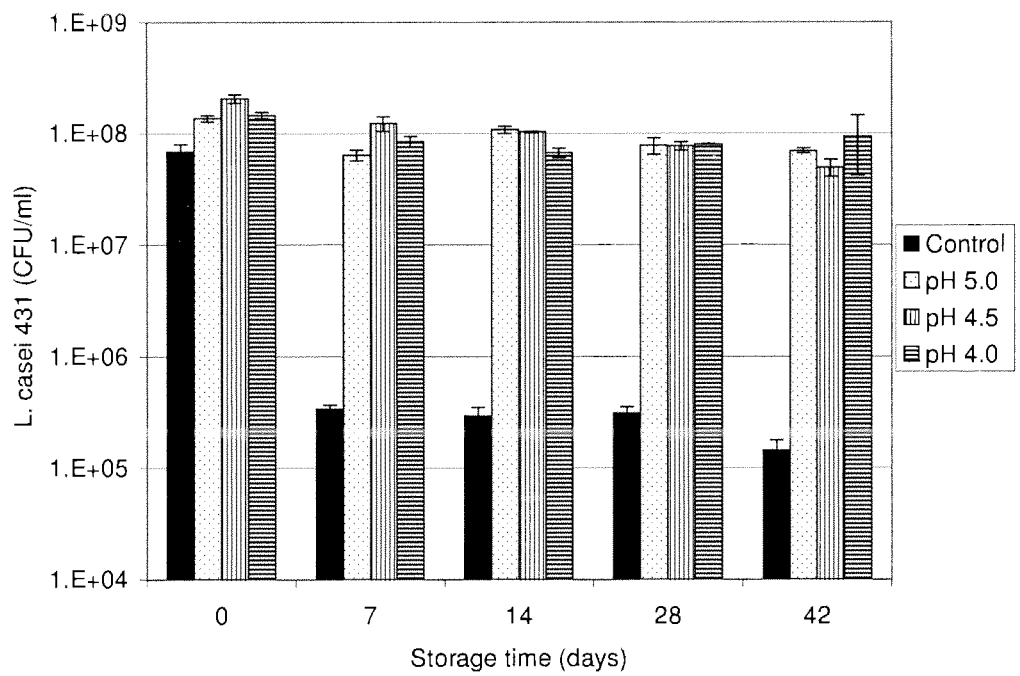
FIG. 6 illustrates cell counts of *L. casei* 431® when added to a 100% orange juice for non-adapted (control), adapted either to pH 4.0, 4.5 or 5.0 during production and then added in concentrations of $1.5\times10^8$ CFU/ml.

As illustrated in FIG. 6, cell counts of L. casei 431® were rather constant when adapted to pH 4.0, 4.5 or 5.0 during production, whereas significant cell count reductions were observed for the non-adapted L. casei 431®.

Example 5

Stability of Adapted L. casei 431 During Frozen Storage

Figure 7:
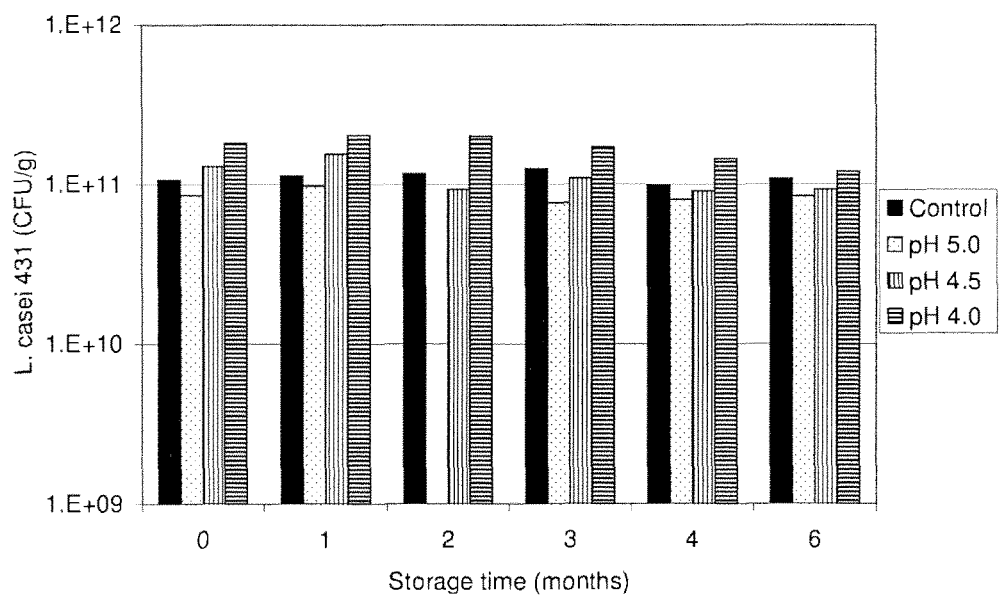
FIG. 7 shows cell counts of *L. casei* 431® non-adapted (control) and adapted either to pH 4.0, 4.5 or 5.0 during production and then stored as frozen pellets at −50° C., and regularly tested for viability on thawn culture by pour plating.

L. casei 431® produced according to example 1 were stored as frozen pellets at −50° C., and regularly tested for viability. Cell counts were determined on thawn culture by pour 5 plating appropriate 10 fold dilutions in MRS agar followed by anaerobic incubation for 3 days at 37° C. As illustrated in FIG. 7, cell counts of both the non-adapted as well as the L. casei 431® adapted to pH 4.0, 4.5 or 5.0 during production were very constant for at least 6 months when stored at −50° C.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Example 6

Survival of L. casei 431® in Juice Following Long-Term Frozen Storage

After 6 months of storage at −50° C. as frozen pellets, survival was determined in 100% 25 orange juice for the batch of L. casei 431 adapted to pH 4.0 during production. F-DVS of the probiotic culture was diluted in saline peptone to ensure that initial cell counts of $10^8$ CFU/ml were obtained by adding an inoculum of 1% (v/v) to cartons of orange juice. As a control, other cartons of 100% orange juice were added the non-adapted L. casei 431® stored for 6 months at −50° C. The juices were stored at 8° C. protected from light and regularly sampled for L. casei 431® cell count determinations by pour plating appropriate 10-fold dilution in MRS agar followed by anaerobic incubation for 3 days at 37° C.

Figure 8:
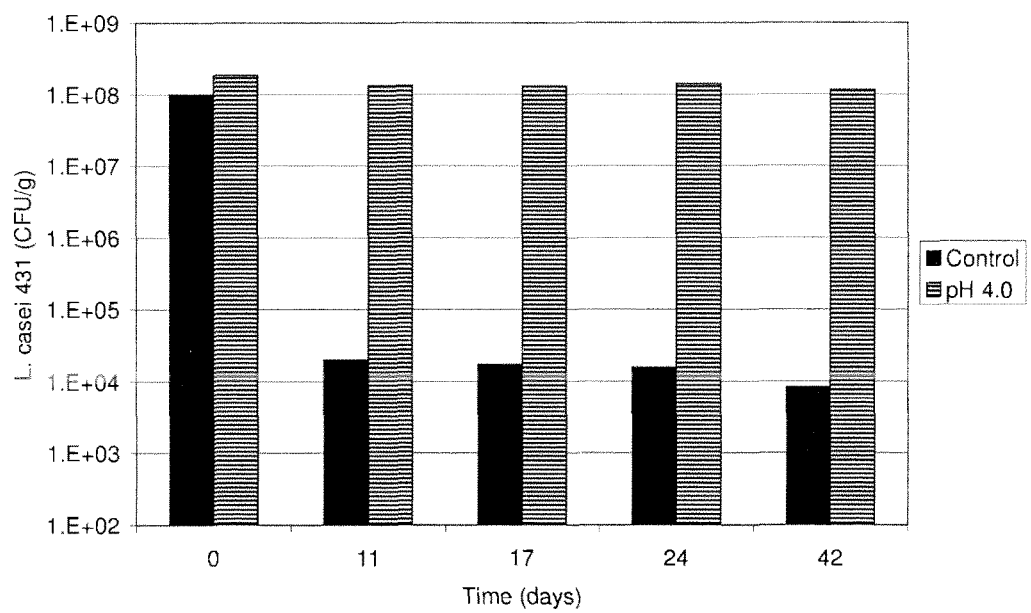
FIG. 8 illustrates cell counts of *L. casei* 431® non-adapted (control) or adapted to pH 4.0 during production, stored as frozen pellets at −50° C. for 6 months and then added to orange juice stored at 8° C. for the time period indicated on the x-axis.

As illustrated in FIG. 8, cell counts of L. casei 431® were rather constant when adapted to pH 4.0 during production, stored for 6 months at −50° C. and then cold-stored in orange juice for 6 weeks. On the contrary, significant cell count reductions were observed for the non-adapted L. casei 431® when stored for 6 months at −50° C. and added to orange juice. This illustrates that the good survival in orange of L. casei 431® adapted to pH 4.0 during production is maintained even after long frozen storage of the culture at −50° C.

Example 7

Long-Term Storage Stability of Adapted L. casei 431® in 100% Orange Juice

L. casei 431® produced according to the procedure described in Example 1 was used for inoculation of 100% orange juice (pH 3.8). F-DVS of the probiotic culture was diluted in saline peptone to ensure that initial cell counts of approx. 1e08 CFU/ml were obtained by adding an inoculum of 1% v/v to cartons of fruit juice. The juices were either inoculated with L. casei 431® adapted to pH 4.0 or as a control, the non-adapted 'control' L. casei 431®. The orange juices were stored protected from light at 8° C. for 70 days and regularly sampled for cell count determination by pour plating appropriate 10-fold dilutions in MRS agar followed by anaerobic incubation for 3 days at 37° C.

Figure 9:
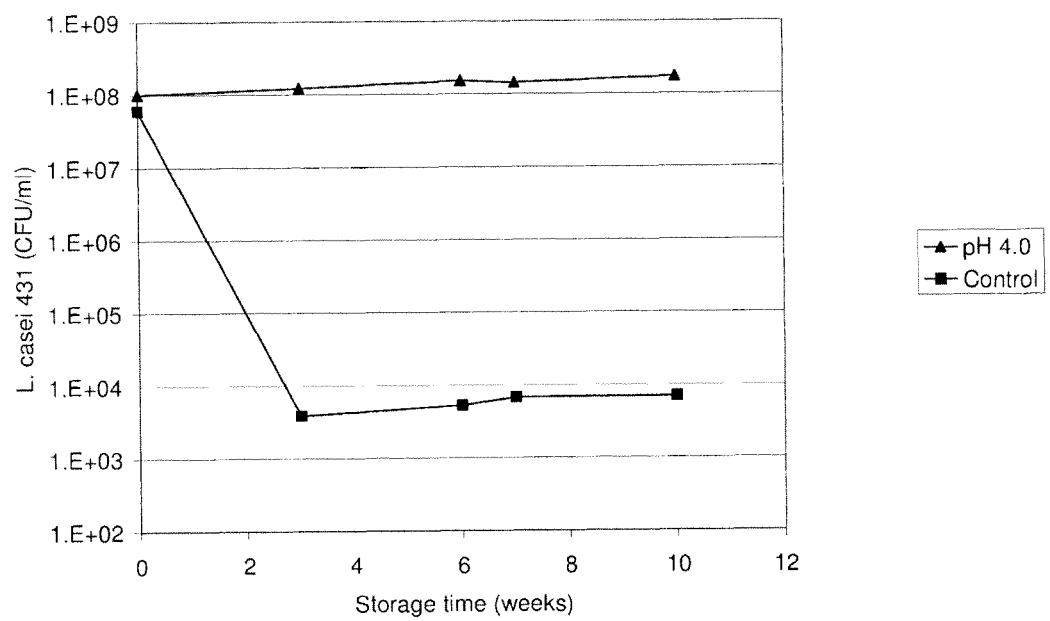
FIG. 9 depicts cell counts of *L. casei* 431® when added to orange juice for non-adapted cells (square), alternatively cells adapted to pH 4.0 (triangle) during production and then stored at 8° C.

As illustrated in FIG. 9, cell counts of L. casei 431® were rather constant when adapted to pH 4.0 during production and then cold-stored in orange juice for up to 10 weeks. On the contrary, significant cell count reductions were observed from the first sampling point at 3 weeks storage for the non-adapted L. casei 431® when cold-stored in orange juice. This illustrates the superior survival of L. casei 431® adapted to pH 4.0 in orange juice even up to 10 weeks cold-storage.

REFERENCES

European Patent EP 0113055
US Patent Application US 2010/0086646
PCT Patent Application WO 2010/132017
All references cited in this patent document are hereby incorporated herein in their entirety by reference.

The invention claimed is:
1. A method for producing a probiotic fruit beverage that does not contain milk, comprising:
(a) acid-adapting at least one strain of probiotic bacteria by propagating the strain without pH stabilization at a temperature of from 25° C. to 43° C., wherein the propagating is in an initial medium having a pH of from about 6.0 to about 7.0, wherein the initial medium does not have dipotassium hydrogen phosphate, and wherein the propagating reduces the pH of the medium to a pH of from about 4.0 to 5.0; and
(b) inoculating a fruit beverage with the at least one strain of acid-adapted probiotic bacteria, thereby producing a probiotic fruit beverage comprising at least one strain of acid-adapted probiotic bacteria, wherein the probiotic fruit beverage does not contain milk.

2. The method of claim 1, further comprising harvesting the at least one strain of acid-adapted probiotic bacteria prior to the inoculating step.

3. The method of claim 1, wherein the initial medium comprises at least 2% sugar and at least 0.4% yeast extract.

4. The method of claim 1, wherein the inoculating comprises inoculating the fruit beverage with from about $1 \times 10^4$ to $1 \times 10^{10}$ CFU/ml of the acid-adapted probiotic bacteria.

5. The method of claim 1, wherein, after storing the produced probiotic fruit beverage for at least 30 days at a temperature of 8° C., at least 50% of the acid-adapted probiotic bacteria remain viable.

6. The method of claim 1, wherein the pH of the produced probiotic fruit beverage is from 3.2 to 4.2.

7. The method of claim 1, wherein the at least one strain of probiotic bacteria is of a genus selected from the group consisting of *Lactobacillus* and *Bifidobacterium*.

8. The method of claim 1 wherein the probiotic fruit beverage comprises from 20% to 99.99% by weight of fruit juice and/or fruit puree.

9. The method of claim 1, further comprising packaging the probiotic fruit beverage.

10. The method of claim 2, further comprising concentrating the at least one strain of acid-adapted probiotic bacteria.

11. The method of claim 2, further comprising freezing or freeze-drying the at least one strain of acid-adapted probiotic bacteria.

12. The method of claim 1, wherein the probiotic bacteria is *Lactobacillus paracasei* subsp. *paracasei* CRL431.

13. A method for obtaining a culture of an acid-adapted probiotic bacterial strain, comprising:
(a) propagating a probiotic bacterium without pH stabilization at a temperature of from 25° C. to 43° C., wherein the propagating is in an initial medium having a pH of from about 6.0 to about 7.0, wherein the initial medium does not have dipotassium hydrogen phosphate, and wherein the propagating reduces the pH of the medium to a pH of from about 4.0 to 5.0; and
(b) harvesting the cells.

14. The method of claim 13, wherein the initial medium comprises at least 2% sugar and at least 0.4% yeast extract.

15. The method of claim 13, wherein the probiotic bacterial strain is of a genus selected from the group consisting of *Lactobacillus* and *Bifidobacterium*.

16. The method of claim 13, further comprising concentrating the cells.

17. The method of claim 13, further comprising freeze-drying the cells.

* * * * *